US007575891B2

(12) United States Patent
Wolfe et al.

(10) Patent No.: US 7,575,891 B2
(45) Date of Patent: Aug. 18, 2009

(54) PROCESS FOR PRODUCTION OF DIPHTHERIA TOXIN

(75) Inventors: Henry Wolfe, Glenmore, PA (US); Fahar Merchant, Edmonton (CA); Rosemina Merchant, Edmonton (CA); Christopher Black, Norristown, PA (US); Harry Storflor, Oslo (NO); Geir Stokke, Oslo (NO); Halldis Hellebust, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 11/854,683

(22) Filed: Sep. 13, 2007

(65) Prior Publication Data

US 2008/0153750 A1 Jun. 26, 2008

Related U.S. Application Data

(62) Division of application No. 11/204,193, filed on Aug. 15, 2005, now Pat. No. 7,273,728, which is a division of application No. 10/690,855, filed on Oct. 22, 2003, now Pat. No. 6,962,803, which is a division of application No. 09/914,162, filed as application No. PCT/GB00/00680 on Feb. 25, 2000, now Pat. No. 6,689,871.

(30) Foreign Application Priority Data

Feb. 26, 1999 (GB) ................................ 9904582.5

(51) Int. Cl.
*C12P 1/00* (2006.01)

(52) U.S. Cl. ........................................................ 435/41

(58) Field of Classification Search .................... 435/41
See application file for complete search history.

(56) References Cited

U.S. PATENT DOCUMENTS

| | | | | |
|---|---|---|---|---|
| 4,925,792 | A | 5/1990 | Rappuoli | |
| 5,087,616 | A * | 2/1992 | Myers et al. | 514/21 |
| 5,728,383 | A | 3/1998 | Johnson et al. | |
| 6,689,871 | B1 | 2/2004 | Wolfe et al. | |
| 6,962,803 | B2 | 11/2005 | Wolfe et al. | |

OTHER PUBLICATIONS

Rappuoli, et.al. "Rapid Purification of Diphtheria Toxin by Phenyl Sepharose and DEAE Cellulose Chromatography" Journal of Chromatography, vol. 268, 1983, pp. 543-548.
Wen, et.al. "Diphtheria Toxin-Related Alpha-Melanocyte-Stimulating Hormone Fusion Toxin" The Journal of biological Chemistry, vol. 266, No. 19, Jul. 5, 1991, pp. 12289-12293.
Zhidkova (Tr. Irkutskogo Nauchn.-Issled. Inst. Epidemiol. I Gigieny (1960) No. 5 pp. 73-76.

* cited by examiner

*Primary Examiner*—Mark Navarro
(74) *Attorney, Agent, or Firm*—Craig Bohlken

(57) ABSTRACT

The present invention provides a method of purifying diphtheria toxin comprising (1) fermenting a microorganism strain capable of producing diphtheria toxin using glucose as a carbon source, said method comprising adding glucose to a growing culture whereby the addition of glucose maintains microorganism growth effective to support diphtheria toxin production; and (2) purifying the diphtheria toxin from the culture by contacting a toxin containing preparation derived therefrom with an ion exchange matrix, eluting a fraction containing the toxin, applying the eluate to a hydrophobic matrix, and eluting a fraction containing the toxin.

2 Claims, 2 Drawing Sheets

GROWTH OF *C. DIPTHERIAE* IN A 10-L FERMENTER IN THE PRESENCE OF DIFFERENT CARBON SOURCES. LOT A, B AND C

GROWTH OF *C. DIPTHERIAE* IN A 10-L FERMENTER IN THE PRESENCE OF 1.5% GLUCOSE. LOT D + CYSTEINE AND 2% YEAST EXTRACT; LOT E + CYSTINE AND 1% YEAST EXTRACT.

PRODUCTION OF CRM107 BY *C. DIPTHERIA* GROWN IN A 10-L FERMENTER IN NIH MEDIUM CONTAINING DIFFERENT CARBON SOURCES LOT A, B AND C ELISA DATA

PRODUCTION OF CRM107 BY *C. DIPTHERIAE* GROWN IN A 10-L FERMENTER IN NIH MEDIUM CONTAINING 1.5% GLUCOSE. LOT D + CYSTEINE AND 2% YE. LOT E + CYSTINE AND 1% YE. (SDS-PAGE)

PROCESS FOR PRODUCTION OF DIPHTHERIA TOXIN

This application is a divisional filing of application Ser. No. 11/204,193 filed Aug. 15, 2005, now U.S. Pat. No. 7,273,728, granted Sep. 25, 2007, which is a divisional filing of application Ser. No. 10/690,855 filed Oct. 22, 2003, now U.S. Pat. No. 6,962,803, granted Nov. 8, 2005, which is a divisional of application Ser. No. 09/914,162 filed Jan. 25, 2002, now U.S. Pat. No. 6,689,871 granted Feb. 10, 2004 which is a 35 U.S.C. § 371 filing of international application number PCT/GB00/00680 filed Feb. 25, 2000 which claims priority to application number 9904582.5 filed in Great Britain on Feb. 26, 1999.

The present invention relates to a process for producing mutant forms of diphtheria toxin, and in particular to a process for producing a non-toxic mutant of diphtheria toxin, for example the mutant known as CRM107, and a toxic conjugate thereof, which can be used for therapeutic purposes.

Diphtheria toxin is a proteinaceous toxin which is synthesised and secreted by toxigenic strains of *Corynebacterium diphtheriae*, i.e. strains which are lysogenic for a bacteriophage carrying the toxin gene. It is initially synthesised as a 535 amino acid polypeptide which undergoes proteolysis to form the toxin which is composed of two subunits, named A and B, joined by a disulphide bond. The A subunit is the enzymatic domain. It catalyses the ADP ribosylation of Elongation Factor 2, thereby inactivating EF-2. EF-2 is an essential enzyme involved in protein synthesis, and its inactivation results in cessation of protein synthesis and death of an ‘infected’ eucaryotic cell. The A subunit is only active intracellularly, but since alone it is unable to bind to or cross the cell membrane it is not toxic when applied extracellularly. It is the B subunit which is responsible for getting the active A subunit into the cells; it does this by binding to the surface of cells by means of a cell surface receptor and then it facilitates the passage of the A subunit across the cell membrane into the cytoplasm where the toxic effects of the A subunit may be exerted.

Diphtheria toxin is highly cytotoxic; a single molecule can be lethal for an ‘infected cell’ and a dose as low as 10 ng/kg can kill animals and humans. There has thus been some considerable interest in investigating therapeutic strategies which utilise the toxic A subunit. The native toxin whilst being highly cytotoxic is non-specific, i.e. it will attack any cell which carries a receptor for the B subunit.

Certain mutant forms of the diphtheria toxin have been reported which are deficient in the cell binding and/or translocation function. These include toxin molecules which have a mutation in the B subunit which results in reduced binding to cells, such as for example mutants CRM9, CRM 45, CRM102, CRM103 and CRM107, as described by Nicholls & Youle in Genetically Engineered Toxins, Ed: Frankel, Marcel Dekker, Inc, 1992. The resulting toxin molecules are essentially non-toxic since the A subunit is unable to reach its site of action. These mutations can have a dramatic effect. Thus CRM107 has an amino acid substitution at position 525, where serine in the native toxin has been replaced by phenylalanine, resulting in a more than 1000 fold reduction in the cell binding property with little or no effect on the translocating properties of the B subunit. The A subunit in such mutants is unaffected, and, if it can be targeted into the cytoplasm, is as toxic as the native toxin.

In designing cytotoxic drugs, there is thus interest in utilising these mutant forms of diphtheria toxin to target specific cell populations without affecting normal cells, by modifying the mutant toxin by linking it in some way to a moiety which is capable of binding to cells, and in particular to a moiety which is specific for certain cells or cell types, such as an antibody to a specific receptor, or a moiety such as a protein for example transferrin, which has a binding partner e.g. in the form of a receptor expressed only or at least predominantly on the surface of cells which are to be killed. In this way, it is possible to harness the cytotoxic properties of the diphtheria toxin A subunit, without affecting, or with only limited effect on, normal cells.

One area where modified forms of mutant diphtheria toxin such as modified CRM107 may be used is in the treatment of certain cancerous conditions, and in particular malignant gliomas. Malignant glioma is the most common CNS neoplasm in adults. No therapy is currently available and prognosis of patients with high grade gliomas, anaplastic astrocytomas and glioblastoma multiforme is thus bleak, with death usually occurring within one year of diagnosis. Mutated diphtheria toxin CRM107, particularly in the form of a targeted conjugate, provides a therapy for conditions such as this, and in particular, conjugates of CRM107 with the iron binding protein transferrin. This is particularly suitable for treatment of tumours including brain neoplasms because transferrin receptors are expressed at a high level on the surface of rapidly dividing cells such as glioma cells, but are absent on the surface of normal brain tissue. Thus mutated diphtheria toxin-transferrin conjugates may be selectively targeted to neoplastic tissue, where the toxin is internalised, and the A subunit kills the ‘infected’ cell.

For clinical use, large quantities of mutant diphtheria toxin are needed. There are however problems in producing diphtheria toxin from toxin producing strains of *C. diphtheriae*, and moreover, difficulties have been encountered in scaling up laboratory scale fermentation conditions to produce sufficient quantities of toxin, and in particular mutant forms of diphtheria toxin, for therapeutic use. Thus there are problems in obtaining toxin in sufficient yield and purity and large scale production thus tends to be inefficient. These difficulties need to be overcome in order to be able to exploit the promise of these so-called targeted mutant toxin derived drugs.

It is known in the art that diphtheria toxin production is dependent on the conditions under which the producing strain is grown. In particular, both iron content of the growth medium and the carbon source which are essential for bacterial growth have been found to have an effect on toxin production. Thus, it has been known for some time that iron in large concentrations has an inhibitory effect upon toxin production, in other words, toxin production is negatively regulated by iron. Thus for toxin preparation, low iron growth media is used, with iron generally in the range of 50-100 μg/l.

Whilst glucose is commonly used as a carbon source for bacterial growth, it has also been known for some time that fermentation of glucose by *C. diphtheriae* can affect diphtheria toxin production. Thus it is known that fermentation of glucose by *C. diphtheriae* can lead to acidic fermentation products including acetic, formic and lactic acid, at least some of which are thought to be bacteriostatic and even possibly bactericidal for the bacteria. Glucose fermentation thus can affect the rate of bacterial growth with corresponding effects on toxin production. It has also been proposed that the acidic fermentation products may have an effect on the stability of the toxin. For this reason, other carbon sources such as maltose and glycerol, used either as the sole carbon source, or as an at least partial substitute for glucose have been used in the art for culturing toxin producing strains of *C. diphtheriae*. Neither of these carbon sources is however as efficient an energy source as glucose.

We have now developed a new fermentation process which enables diphtheria toxin to be produced by *C. diphtheriae* in good yield utilising glucose as the carbon source.

Thus viewed from one aspect, the present invention provides a method for the production of diphtheria toxin wherein a microorganism capable of producing diphtheria toxin is fermented using glucose as a carbon source, said method comprising adding glucose to a growing culture whereby the addition of glucose maintains a microorganism growth effective to support diphtheria toxin production.

As used herein, the term 'diphtheria toxin' is used to refer to the naturally occurring protein, as well as mutated forms, particularly for therapeutic purposes mutated forms of the B subunit which have reduced or no binding function whilst retaining at least a degree of translocation function and preferably retaining at least some A subunit enzymatic activity, variants for example proteins which have amino acid substitutions, additions or deletions and fragments thereof, particularly fragments which retain the cytotoxic activity of the A subunit. The method of the invention may be used to prepare the naturally occurring diphtheria toxin, as well as mutant forms, such as the aforementioned non-toxic mutants such as CRM107.

The naturally occurring diphtheria toxin may be obtained from toxin producing strains available from a variety of publicly available sources including the American Type Culture Collection. CRM 107 may be obtained from the strain *Corynebacterium diphtheriae* monolysogen C7 $\beta^{tox\ 107}$, which is obtainable from National Institutes of Health, 6011 Executive Boulevard, Rockville Md. 20852, USA (Dr Richard Youle). Mutant forms of the toxin, such as the mutant forms described by Laird et al, J. Virology, 19, 220-227, 1976, and by Nicholls & Youle in Genetically Engineered Toxins, Ed: Frankel, Marcel Dekker, Inc, 1992, including CRM107, may also be prepared by methods known in the art, for example by the methods described in Laird et al (supra) or by expression in *C. diphtheriae* or other microorganisms using the techniques of recombinant DNA technology (Sambrook et al, Molecular Cloning, a Laboratory Manual, Cold Spring Harbor Laboratory Press, 1989), and also by site directed mutagenesis, based on the known nucleotide sequence (Greenfield et al, Proc Nat Acad Sci 50, 6953-7, 1993) of the wild type structural gene for diphtheria toxin carried by corynebacteriophage β.

In the method of the invention, glucose is added as required to a growing culture, preferably an exponential culture, more preferably a late exponential phase culture, and/or may be added as required to a growing culture in stationary phase, preferably a batch fermentation culture.

This method contrasts with conventional batch fermentation, wherein an initial supply of nutrients is not renewed, and thus the culture grows exponentially for only a few generations until an essential nutrient is exhausted, and with conventional continuous culture in which fresh growth medium is added continuously at a constant rate whilst culture is simultaneously removed resulting in much longer exponential growth periods.

The fed batch method according to the invention offers an advantage over prior methods which utilise glucose as a carbon source for growth of *C. diphtheriae* and synthesis of toxin. Thus for example, Fass et al., Appl. Microbiol. Biotechnol. 43, 83-88 (1995) describe a two stage process in which glucose and iron are simultaneously depleted at the end of the exponential growth phase, and toxin is thus produced only once the culture enters stationary phase. In contrast, the controlled glucose addition in accordance with the invention enables toxin to be produced during the late exponential phase as well as during the stationary phase by prolonging the late exponential and early stationary phases, and as a result enables toxin to be produced and accumulated for a longer time thereby increasing the cumulative toxin production capacity of a culture.

The method may be used to produce diphtheria toxin both from its natural producer, *C. diphtheriae* and also from other microbial hosts, such as bacteria for example *E. coli* transformed with toxin genes or modified toxin genes.

The fed batch fermentation method is particularly applicable for the production of diphtheria toxin by toxin producing strains of *C. diphtheriae* because of the inhibitory effect which certain nutrients or their metabolites may have on toxin production, if their concentration is not controlled carefully. The fed batch method of the invention thus enables a low level of glucose to be maintained in the medium whilst at the same time providing the necessary carbon source required for growth. Thus by carefully monitoring the levels of glucose and/or pH of the fermentation culture, glucose levels may be controlled to achieve a balance between on the one hand providing sufficient and efficient carbon source to support bacterial growth, and toxin production, and on the other hand limiting the generation of inhibitory fermentation by-products which can have a detrimental effect on toxin production. By adding glucose to the fermentation medium as required during the fermentation, the pH can be controlled using the organic acids produced from glucose metabolism without the additional complication of adding exogenous inorganic acid, whilst enabling toxin to be produced during both the exponential and stationary growth phases. Thus glucose can be used both as a source of acid and as a carbon source to increase cell density.

In the method of the invention, growth is initiated in a glucose-based medium comprising conventional levels of glucose, for example within the range 0.8 to 2.5% such as about 1.5% glucose. The improvement over the prior methods is that glucose is added to the culture medium during the fermentation, commencing during the exponential growth phase or during the stationary phase at such time as is required to maintain the pH within a range optimal for microorganism growth and toxin production, preferably from 7.0 to 7.5, preferably from 7.1 to 7.3, for example at around 7.2. As mentioned above, certain acidic substances are by products of glucose metabolism, and these acids assist in controlling the pH of the fermentation medium.

If necessary, the pH may additionally be controlled by addition of acid or base as appropriate to maintain the pH of the culture at an appropriate level for toxin expression, for example at about pH 7.2±0.2.

Thus we have found that by controlling the glucose concentration within the fermentation culture by periodic addition to maintain the pH within the aforementioned range, it is possible to maximise cell growth and toxin production by minimising toxin degradation due to fluxes in pH. Thus we have observed that as the *C. diphtheriae* cells enter the logarithmic growth phase, pH and glucose concentration decreases. We have also found that the purity of the toxin decreased as the pH of the medium decreased. Without wishing to be bound by theory, it is believed that this might be due to proteolytic breakdown. Toxin purity was also observed to decrease as fermentation progressed at pH's below about 7, and also at pH's in excess of about 8.0. It is for this reason that the glucose (and the pH levels determined thereby) levels are desirably maintained within this range.

The progress of fermentation may be monitored by measuring various parameters indicative of bacterial growth and toxin production either in samples aseptically removed from the culture vessels or by direct measurement in the fermentation broth. For example pH may be monitored within the fermentation broth by means of a pH probe. Glucose may be monitored by a variety of methods known in the art, either directly or indirectly, for example methods described in clinical Diagnosis and Management by Laboratory Methods, 18 Edn, John Bernard Henry, Editor, WB Saunders Company, Philadelphia, 1991. Examples of direct measurement include sugar assays for example those based on chemical reactions such as for example enzymic reactions, for example reactions based on the use of glucose oxidase, such as calorimetric reactions. Examples include measurement by means of dipsticks for example glucose chemstrip BG from Boehringer Mannheim and use of an on-line glucose monitor. Since pH has been shown to decrease in proportion to glucose consumption, glucose may also be monitored indirectly by monitoring pH of the broth. Toxin production may be monitored in a variety of known ways, such as for example, SDS PAGE (Laemmli, Nature 227, 680-684, 1970), ELISA (Nielsen et al, Journal of Clinical Microbiology, 25, 1280-1284, 1987) or an ADP-ribosylation assay (Blanke et al., Biochemistry 33, 5155 (1994) or by a combination of these methods. Generally, glucose addition will commence when the level of glucose in the medium drops to levels such that, but for the addition of glucose to generate acidic byproducts, acid would need to be added to control the pH of the fermentation medium. Generally, additional glucose may be added when the level of glucose in the fermentation medium drops below about 10 g/L, preferably below 2 g/L and more particularly below about 1 g/L. At this level, the exponential growth phase of the culture is extended and the pH of the media decreased by increased metabolism of glucose. In this way, glucose feeding may be used to control pH and stabilise the toxin as well as to maintain growth of culture to obtain high cell density.

We have thus found that with the glucose fed batch fermentation method according to the invention, in a culture medium comprising 10-15 g/L glucose, the exponential phase of bacterial growth commences generally 5 hours after the start of fermentation, with toxin production starting within approximately 9 hours after the start of fermentation. With periodic addition of glucose commencing generally 8 hours after the start of fermentation, such as about 9 hours, for example when the culture is in the last 25% increase in growth curve OD value, we have been able to achieve toxin production for at least 13.5 hours. In such a fed batch method, additional glucose in the range of 7 g/L to 15 g/L may be consumed.

By the fed batch glucose feeding method of the invention, we have been able to achieve a cell density in the range of 45-60 (OD at 590 nm) and a toxin production in the range of 145-165 mg/ml culture.

In addition to a carbon source, there are other minimum nutritional requirements for growth of *C. diphtheriae*. These include trace metals, phosphate and a nitrogen source. Generally casamino acids and yeast extract are included in bacterial growth media to provide a nitrogen and amino acid source. Growth media for *C. diphtheriae*, such as CY medium (Fass et al., Applied Microbiol. Biotechnol. 43, 83-88 (1995)) generally contains at least 2% yeast extract. We have however found that increasing the carbon to nitrogen ratio by reducing the amount of yeast extract below this conventional level, to between 0.5-1.5% such as between 0.75 to 1% for example around 1% yeast extract, improves the fed batch fermentation method according to the invention. Thus we have found that reducing the conventional amount of yeast extract results in a significant improvement in yield of toxin. We have also found an improvement in yield can be obtained by using cystine as opposed to cysteine which can be used in bacterial growth media. Thus a 5-fold increase in yield of CRM107 has been observed when using 1% yeast extract and using a medium containing 0.7 g/l cystine as compared to 2% yeast extract in a medium containing 0.26 g/l cysteine in a 10 litre fermentation according to the invention.

Accordingly, the use of a growth medium containing no more than 1% yeast extract constitutes a preferred aspect of the method of the invention.

We have found that the reduced yeast extract fermentation conditions also have other benefits in addition to increased toxin yield in diphtheria toxin production. Thus as will be described in more detail below, reducing the yeast extract content of the growth medium has additional benefits in purification of the toxin.

The present invention also relates to a method for purifying diphtheria toxin from a culture supernatant of a toxin producing bacterial strain.

Diphtheria toxin is secreted in large quantities from synthesising bacteria such as corynebacteria; it can reach up to 70% of the total protein in the culture medium. This level is sufficiently high that for small, laboratory scale cultures, a straightforward precipitation for example using ammonium sulphate or trichloroacetic acid of the culture medium may be effective alone to purify the toxin. However, difficulties are encountered when using large scale cultures. The precipitation steps are time consuming and due to difficulties in handling and dialysing such large volumes of material, there is loss of toxin product. We have now developed a purification method which is capable of handling large volumes of material and overcomes these disadvantages.

Thus viewed from a further aspect, the present invention provides a method of purifying diphtheria toxin from a culture of toxin producing bacteria, said method comprising contacting a toxin containing preparation with an ion exchange matrix, eluting a fraction containing the toxin, applying the eluate to a hydrophobic matrix, and eluting a fraction containing the toxin.

The starting material for purification may for example be a toxin containing supernatant, a toxin containing cellular fraction or a toxin containing preparation derived from a culture supernatant, for example a concentrated supernatant, such as an ultrafiltered supernatant, or a diafiltered supernatant.

In toxin purification methods known in the art, the ion exchange step is performed after the hydrophobic interaction chromatography step, because the art taught that culture supernatant cannot be directly applied to an ion exchange matrix, such as DEAE cellulose. Such matrices are capable of binding proteins only under conditions of low ionic strength, and it has thus been thought that the ionic strength of culture medium would be too high to achieve efficient binding (Rappuoli et al, J. Chromatography, 268, 543-548, 1983).

We have however found that contrary to this perception in the art, it is indeed possible to apply a culture supernatant onto an ion exchange matrix, such as immobilised DEAE. Preferably, because toxin generally binds to ion exchange media at low ionic strength, the culture supernatant is diafiltered prior to applying to the matrix, for example in the form of a column. This has enabled the two chromatographic separation steps to be operated in the sequence of ion exchange chromatography (IEC) before hydrophobic interaction chromatography (HIC). In addition, diafiltration may serve as a purification step.

Thus viewed from another aspect, the present invention provides a method of purifying diphtheria toxin from a culture of toxin producing bacteria said method comprising chromatographic steps of ion exchange chromatography and hydrophobic interaction chromatography, characterised in that said method comprises carrying out an ion exchange chromatography before hydrophobic interaction chromatography.

We have found that this purification method according to the invention results in a higher toxin yield as compared to the conventional process, without sacrifice to purity (i.e. without significant levels of contaminating proteins). Thus we have found that by carrying out an IEC step before HIC, a purity of up to around 98% can be achieved.

Preferably, the starting material is a culture supernatant for example a culture supernatant from a culture which is fermented using glucose as a carbon source in accordance with the invention. As mentioned above, the use of lower amounts of yeast extract than is conventional at least in glucose culture media, for example about 1% has additional advantages besides improved yield. Thus we have observed that yeast extract contributes to pigmentation of the growth medium, contributing to contaminants which can make the subsequent purification process less effective. Accordingly, the ability to reduce the levels of contaminants at the outset represents an advantage for subsequent purification. Culture media with lower yeast content are less pigmented, and accordingly advantageous.

Thus viewed from a further aspect, the present invention provides a method of purifying diphtheria toxin comprising (1) fermenting a microorganism strain capable of producing diphtheria toxin using glucose as a carbon source, said method comprising adding glucose to a growing culture whereby the addition of glucose maintains microorganism growth effective to support diphtheria toxin production; and (2) purifying the diphtheria toxin from the culture by contacting a toxin containing preparation derived therefrom with an ion exchange matrix, eluting a fraction containing the toxin, applying the eluate to a hydrophobic matrix, and eluting a fraction containing the toxin.

Preferably, the microorganism is a bacteria, such as *C. diphtheriae*. In the case of *C. diphtheriae*, where toxin is secreted into the culture supernatant, the method may be carried out directly on culture supernatant or on a preparation derived therefrom such as for example a diafiltered culture supernatant. Thus a preliminary step may involve a primary clarification of the culture broth to obtain a toxin-containing culture supernatant. Thus bacteria may be separated from the culture broth by methods known in the art, such as centrifugation or filtration, for example, ultrafiltration, and the resulting supernatant diafiltered or applied directly to the first matrix, the ion exchange matrix. In the case of expression in other microorganisms, such as *E. coli* genetically modified with toxin, toxin may be found intracellularly, for example in the periplasm or cytoplasm. In such cases, primary recovery steps may depend upon the cellular location. The toxin may be extracted from the cells by methods known in the art, for example as described by Skopes in Protein Purification, Principles and Practice, 3rd edn, Pub: Springer Verlag, followed by purification in accordance with the method of the invention.

Filtration to clarify the fermentation broth may be effected by methods known in the art, for example with membranes such as hollow fibre or spiral wound membranes, such as by means of a 0.1 or 0.2 μm filter, for example a hollow fiber filter, such as that obtainable from A/G Technology, or a 0.4 or 0.65 μm hollow fibre or spiral wound membrane, or a 300K or 500K filter.

For ease of handling, particularly where large volumes are concerned, such as would be the case for 'industrial' scale purification for pharmaceutical purposes, a degree of concentration of the supernatant may be effected prior to the ion exchange step. The cell free culture supernatant may be concentrated, generally 5 to 50 fold, preferably 15 to 25 fold, such as 20 fold, using protein concentration methods known in the art, for example by means of ultrafiltration with porous materials for example in the form of filters, membranes or hollow fibres. For ease of handling, filters are preferred. For ultrafiltration/concentration, filters having a molecular weight cut off smaller, preferably 20% smaller than the toxin, are preferred, preferably 30K filters (i.e. filters which have a 30000 dalton molecular weight cut off). Suitable materials for such filters are known in the art and include polymeric materials such as mixed cellulose, polyether sulfone or PVDF, for example polysaccharides such as cellulose, and polysulfones. Preferred materials are those which have a lower capacity or ability to absorb toxin. Cellulose filters are particularly preferred, for example filters made from regenerated cellulose such as the 'YM' based filters and other membranes which have little protein binding capacity for example the Flat plate tangential flow bioconcentrators produced by Amicon. The use of cellulose filters for ultrafiltration thus constitutes a preferred aspect of the purification method according to the invention.

IEC may be carried out directly on the culture supernatant, using an appropriately sized bed volume as determined by one skilled in the art. Optionally, the concentrated clarified supernatant may be further treated prior to chromatographic purification, for example by diafiltration. In this way, ionic strength may be reduced by removing salts and other ions smaller than the molecular weight cut off size of the diafiltration membrane. The reduction in ionic strength has benefits for the ensuing ion exchange step, since at reduced ionic strength, less toxin is retained by the ion exchange matrix and yield is thus improved. Furthermore, a partial purification is achieved by the diafiltration membrane. Diafiltration may thus be carried out against a low ionic strength buffer, for example Tris, Tricine, MES, Bis-Tris, TES, MOPS and phosphate, in a concentration of from about 0.1 mM to about 100 mM, preferably from about 10 to about 50 mM, for example 10 mM, having a pH of from about 5 to about 8, preferably from about 6 to about 8 for example about 7.4 to 7.6, using for example a 30 000 cut off membrane which will result in removal of salts, low molecular weight media components and secreted proteins less than 30 000 dalton molecular weight. Such components may otherwise bind to the ion exchange matrix and reduce its capacity to bind toxin. Diafiltration may be carried out for example using materials of the type used for the ultrafiltration step, against buffers such as low ionic strength buffers such as Tris, Tricine, MES, BiS-Tris, TES, MOPS or phosphate, in a concentration of from about 0.1 mM to about 100 mM, preferably from about 10 to about 50 mM, for example 10 mM, having a pH of from about 5 to about 8, preferably from about 6 to about 8 for example about 7.4 to 7.6, for example 10 mM potassium phosphate pH 7.6 so as to reduce the conductivity of the concentrated culture supernatant as low as possible, preferably below about 5 mS/cm.

Treatment of the culture supernatant in this way prior to IEC thus overcomes the problems of the prior art method which requires that HIC has to take place before IEC. The combination of diafiltration and ultrafiltration not only reduces the ionic strength, but serves as an initial purification and allows the volume to be reduced. This means that smaller columns may be used, thereby reducing the time required for the chromatographic steps to be carried out.

A further advantage is that toxin purification according to the method of the invention is faster overall than the conventional method, thus limiting the time during which the toxin is exposed to room temperature and vulnerable to degradation.

The chromatographic steps may be carried out using ion exchange or hydrophobic matrices as appropriate in batch or column form, the latter being preferred for both speed and convenience. The matrix may be a conventional support as known in the art for example inert supports based on cellulose, polystyrene, acrylamide, silica, fluorocarbons, cross-linked dextran or cross-linked agarose.

Any conventional ion exchange resin may be used. Examples include Q sepharose and diethylaminoethyl (DEAE) and quaternary amine resins. The anion exchange material may be packed into a column, whose size will be dependent upon the volume of culture supernatant to be used. The appropriate column size may be determined by those skilled in the art according to the total protein in the concentrated media. Generally, for large scale cultures of the order of 40-50 litres, 2 litre supernatant concentrates may be applied to columns of volume 1.25 l. The column may first be equilibrated with a buffer for example a low ionic strength buffer such as Tris, Tricine, MES, Bis-Tris, TES, MOPS or phosphate, in a concentration of from about 0.1 mM to about 100 mM, preferably from about 10 to about 50 mM, for example 10 mM, having a pH of from about 5 to about 8, preferably from about 6 to about 8 for example about 7.4 to 7.6, for example the buffer used to diafilter the concentrated supernatant, such as 10 mM potassium phosphate pH 7.6. The culture supernatant or concentrate may then be loaded, the column washed with a buffer of low ionic strength and the same pH as the equilibration buffer to wash off any unbound protein, for example the equilibration buffer.

Bound toxin may then be eluted in a variety of ways. These include altering the pH or increasing the ionic strength of the buffer. Thus toxin may be eluted by a gradient increase of buffer with high ionic strength, such as Tris, Tricine, MES, Bis-Tris, TES, MOPS or phosphate, in a concentration of from about 10 mM to about 1.0 M, preferably from about 10 mM to about 500 mM, containing salts like NaCl, KCl or ammonium sulphate at a concentration of from about 0.1M to 1.0M. These buffers may have a pH of from about 5 to about 8, preferably from about 6 to about 8 for example about 7.0 to 7.6. One example of a preferred buffer is 10 mM potassium phosphate containing 500 mM KCl at pH 7.6. The protein will be eluted between 100 to 150 mM KCl in the buffer.

The toxin containing eluate may then be applied to the hydrophobic matrix. Optionally but preferably, the ionic strength of the eluate may be increased prior to the second hydrophobic interaction step, by mixing with a buffer of appropriate ionic strength or by diafiltration. This may facilitate binding of toxin to the hydrophobic resin. Thus the eluate may be mixed with a high ionic strength buffer for example Tris, tricine, MES, Bis-Tris, TES, MOPS or phosphate, in a concentration of from about 10 mM to about 1.0M, preferably from about 10 mM to about 500 mM, containing salts like NaCl, KCl or ammonium sulphate at a concentration of about 0.1M to 1M. The buffers may have a pH of from about 5 to about 8, preferably from about 6 to about 8 for example about 7.0 to 7.6. One example of a preferred buffer is 10 mM potassium phosphate buffer containing 500 mM ammonium sulphate with a pH of 7.0. Diafiltration may be carried out using methods known in the art, for example using ultrafiltration membranes, such as 30K or 10K cut off hollowfibre filters obtainable from A/G technology or spiral wound filters from Amicon, or Ultrasette (Omega) (Pall Filtron) and using buffers such as the aforementioned tris, phosphate, acetate or HEPES.

Hydrophobic matrices are known in the art. These include the aforementioned supports carrying hydrophobic moieties such as alkyl, for example butyl, hexyl, octyl, acetyl or phenyl groups, for example alkyl agarose such as decyl agarose.

The hydrophobic matrix material may be packed into a column, whose size will be dependent upon the volume of culture supernatant to be used. The appropriate column size may be determined by those skilled in the art. Generally, for large scale cultures of the order of 40-50 litres, the eluate from the IEC step will be generally in a volume of 1 l to 2 l and will be applied to columns whose size may be determined by those skilled in the art according to the amount of protein, but may be of the order of 250 ml for protein concentration of up to 100 mg/ml. The column may first be equilibrated with a high ionic strength buffer, for example Tris, Tricine, MES, Bis-Tris, TES, MOPS or phosphate, in a concentration of from about 10 mM to about 1.0 M, preferably from about 10 mM to about 500 mM, containing salts like NaCl, KCl or ammonium sulphate at a concentration of about 0.1M to 1.0M, having a pH of from about 5 to about 8, preferably from about 6 to about 8 for example about 7.6, for example the buffer used to diafilter the concentrated supernatant or the buffer mixed with the eluate, such as for example 50 mm potassium phosphate with 1M ammonium sulphate pH 7.0. The IEC eluate, or eluate mixed with high ionic strength buffer or diafiltered eluate may then be loaded, the column washed with a high ionic strength buffer for example Tris, Tricine, MES, Bis-Tris, TES, MOPS or phosphate, in a concentration of from about 10 mM to about 1.0 M, preferably from about 10 mM to about 500 mM, containing salts like NaCl, KCl or ammonium sulphate at a concentration of about 0.1 M to 1.0 M, having a pH of from about 5 to about 8, preferably from about 6 to about 8 for example about 7.6, such as for example the column equilibration buffer to remove any unbound proteins. Bound toxin may then be eluted in a variety of ways for example by gradient increase of a polar solvent in the wash buffer or by gradient increase of a low ionic strength buffer, for example Tris, Tricine, MES, Bis-Tris, TES, MOPS or phosphate, in a concentration of from about 10 mM to about 1.0 M, preferably from about 10 mM to about 500 mM, containing salts like NaCl, KCl or ammonium sulphate at a concentration of about 0.1M to 1.0M, having a pH of from about 5 to about 8, preferably from about 6 to about 8 for example about 7.6, for example 50 mM phosphate containing 1M ammonium sulphate pH 7.0 to 50 mM phosphate buffer pH 7.0 without ammonium sulphate. Toxin may be eluted in such a gradient as the ammonium sulphate concentration is reduced to approximately 700 mM.

By using the method of the invention, we have been able to purify diphtheria toxin mutant CRM107 from large volumes of culture supernatant, of the order of 50 l with an average yield of 32% of the starting material and purity greater than 98% as measured by HPSEC (high performance size exclusion chromatography). This for the first time enables the properties of diphtheria toxin mutants such as the binding mutant CRM107 to be exploited for preparing therapeutic products.

When the purified toxin is a mutant toxin to be used to prepare targeted toxin derived therapeutic agents, the toxin may conveniently be eluted with a buffer suitable for carrying out the conjugation or attachment of the toxin with a cell specific binding or targeting moiety, for example a cell recognition moiety such as an antibody to a cell surface moiety or an antigen binding fragment thereof or a protein which has a binding partner on the cell surface for example in the form of a receptor, such receptors having some degree of selectivity, i.e. being present on some but not all cell types.

As used herein, 'cell specific' or 'cell selective' refers to a moiety which has a targeting or binding affinity for a cell surface moiety which is not present on all cells, and thus which is selective for certain cells or groups or types of cells or specific receptors. In other words, it encompasses a moiety which enables a diphtheria toxin or mutant toxin conjugated to it to be targeted selectively.

Thus according to a further aspect, the present invention provides a process for preparing a diphtheria toxin conjugate comprising linking a diphtheria toxin produced by the method of the invention with a cell specific binding or targeting moiety.

Examples of cell specific moieties include antibodies to moieties exposed on the surface of particular cells, and proteins such as growth factors or transferrin whose binding partners in the form of receptors are expressed only on particular cell types, or predominantly only on specific cell types.

Conjugation may be effected by methods known in the art such as chemical cross-linking or covalent bond formation. Preferably the conjugation is be means of covalent bond formation for example between maleimido groups introduced onto one component of the conjugate and thiol groups introduced onto the other. In such a method, one of the two components is modified by introduction of maleimide groups and the other is modified by means of introduction of thiol groups. Preferably the diphtheria toxin or mutant is modified by means of maleimide groups and the cell specific targeting moiety by means of thiol groups. Preferably for the preparation of anticancer agents such as those for the treatment of malignant glioma, the cell selective moiety is transferrin since transferrin receptors are expressed in quantity in rapidly dividing cells such as glioma cells but are essentially absent on other cells in the CNS. In such conjugates, generally the diphtheria toxin element is modified with maleimide and the transferrin element with thiol groups. However, diphtheria toxin element may be modified with thiol groups and the transferrin element with maleimide.

Conventional modifying agents known in the art may be used. Examples include esterifying compounds, thiol activating compounds and carboxyl modifying agents such as N ethyl maleimide and maleimidobenzoyl-N-hydroxysuccinimidyl ester (MBS) and 2-iminothiolane. In a typical conjugation, MBS may be added to diphtheria toxin in a ratio of from 1 to 100 times molar excess, such as 2 to 5 preferably 3.5 times, incubated at a temperature of 2 to 50° C. for example 15 to 20° C. such as room temperature, for 5 minutes to 24 hours, such as from 20 to 40 minutes such as 30 minutes followed by removal of excess reagent by techniques known in the art such as gel filtration for example using Sephadex G-25 desalting. The eluate may then be cooled prior to the conjugation reaction. Crude intermediates may be removed prior to conjugation by methods known in the art such as precipitation, dialysis, chromatography, extraction. Transferrin may be thiolated by means of incubation with 2-iminothiolane in a ratio of 1 to 100 times molar excess, such as 5 to 10 times molar excess preferably 7 to 8 times such as 7.7 times at a temperature of 2 to 50° C., for example 35-40° C., for 5 minutes to 24 hours, such as 20 to 40 minutes such as 30 minutes followed by removal of excess reagent by techniques known in the art such as gel filtration. For the conjugation, the two functionalised reagents may be mixed in a ratio of 1 to 2 preferably at a temperature of 2 to 8° C. for 4 to 24 hours, preferably 12 to 20 hours, for example 18 hours.

According to a yet further aspect, the present invention provides a method of treatment of a CNS neoplasm comprising administering to a subject a diphtheria toxin conjugate produced by the method of the invention.

According to a still yet further aspect, the present invention provides the use of a diphtheria toxin conjugate produced by the method of the invention in the manufacture of a medicament for use in the treatment of CNS neoplasm.

Figure 1A:
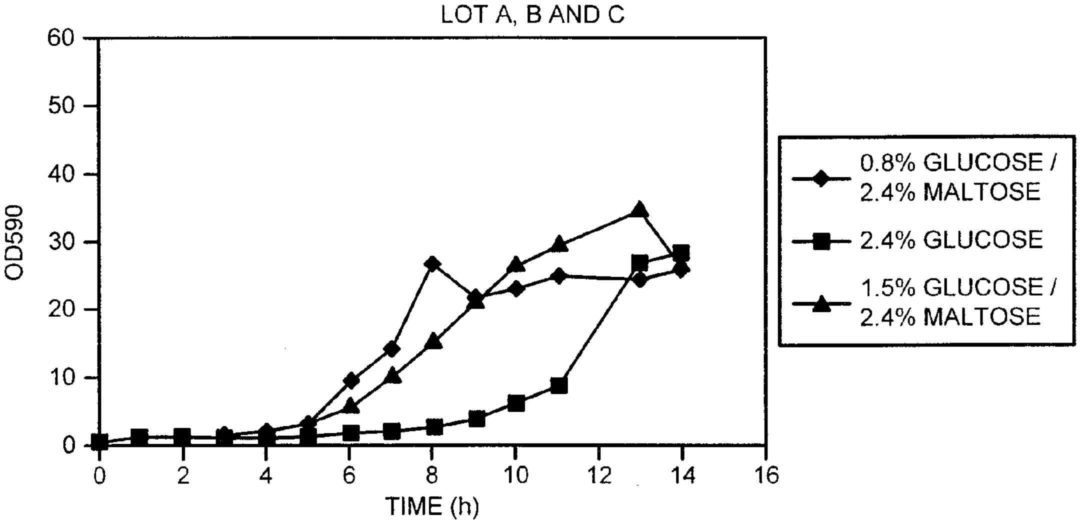
FIG. 1A shows the growth results in batch fermentation lots, using 0.8% glucose/2.4% maltose (A), 2.4% glucose (B) and 1.5% glucose/2.4% maltose (C).

The invention will now be described with reference to the following non-limiting examples.

EXAMPLE 1

Comparison of Batch and Fed Batch Growth

This study was carried out in a 10-L fermenter. Three batch fermentations were investigated, using 0.8% glucose/2.4% maltose (A), 2.4% glucose (B) and 1.5% glucose/2.4% maltose (C). Two fed-batch processes were investigated, using 1.5% glucose as the starting concentration with a glucose feed, in media containing 2% yeast extract and 0.26 g/l cysteine (D) and 1% yeast extract and 0.7 g/l cystine (E).

Methods

Media Preparation

The composition of the five media analysed are shown in Table 1, showing variations in the type and amount of the carbon source, the amount of yeast extract and substitution of cysteine for cystine. The media were based on NIH medium (which comprises 20 g/L yeast extract, 20 g/L casamino acids, 5 g/l $KH_2PO_4$, 15 g/L glucose, 0.7 g/l cystine, 0.1 g/L tryptophan, 1.5 mg/L beta alanine, 1.5 mg/L nicotinic acid, 0.075 mg/L pimelic acid, 0.03 ml of 10 mM HCl, and 10 ml/l metals supplement solution at pH 7.4).

Strain

All examples were carried out using *Corynebacterium diphtheriae* (β $tox^+$) producing CRM107 $Phe^{390}$ $Phe^{525}$ as described by Greenfield et al, Science 238, 536-539, 1987.

Inoculum Preparation

The inoculum for (A) was grown in 100 mL of LICY medium (Mueller et al, J. Immunol 40, 21-32, 1941) in 500 mL flasks, supplemented with glucose at the concentration of 0.8% (w/v). The cultures were incubated at 34±2° C. at 300±50 rpm for 14.5 hours, at which time the $OD_{590}$ was 11.5 and the fermenter was inoculated to a 1.5% (v/v) inoculum.

The inoculum for (B) and (C) was prepared as follows: Two vials containing 1.0 mL of a glycerol frozen culture of *Corynebacterium diphtheriae* (β $tox^+$), were inoculated into a 500 mL flask containing 100 mL±10.0 mL of sterile LICY (NM5) media and incubated at 34±2° C. at 300±50 rpm. The above was carried out in triplicate, which included a back-up inoculum culture. After 15 hours of incubation, the optical density and a Gram stain of the shake flask contents were performed. The optical density at 590 nm of the pooled cultures was 3.4 and 3.9. The Gram stain showed Gram positive rods that were mostly club shaped, indicative of *C. diphtheriae*. The fermenters were inoculated to a 5% (v/v) inoculum with these pooled cultures.

The inoculum for (D) and (E) were prepared as follows: Two vials containing 1.0 mL of a glycerol frozen culture of *Corynebacterium diphtheriae* (β $tox^+$), were inoculated into each of 2.8 L Fernbach flask containing 250 mL±10.0 mL of sterile LICY (NM5) media without a carbon source in duplicates, and incubated at 34±2° C. at 300±50 rpm. One of the flask contained cysteine with 2% yeast extract (for the inoculation of D) and the other contained cystine with 1% yeast extract (for the inoculation of E). Additional inocula for the two fermentations were prepared in three 500 mL flasks each, to enable a pooled inoculum size of 5% (v/v) into the production fermenter. These were prepared from 300 μL of glycerol frozen culture of *Corynebacterium diphtheriae* (β $tox^+$), were inoculated into a 500 mL flask containing 100 mL±2.0 mL of sterile media identical to the fermentation media without the carbon source, and were incubated at 34±2° C. at 300±50 rpm. Back-up inoculum cultures were prepared in triplicate in 500 mL flasks as above but in media containing 1.5% glucose. After 15 hours of incubation, the optical density and a Gram stain of the shake flask contents were performed. The optical density at 590 nm of the cultures was 3.01 and 1.62 for D and E, respectively. Gram stain showed Gram positive rods that were mostly club shaped, indicative of *C. diphtheriae*. The fermenters were inoculated to a 5% (v/v) inoculum with these.

In-Process Monitoring

Samples were taken at one hour intervals. Every hour, the date, actual time, temperature, pH, and agitation were recorded. Residual fermentation medium glucose concentration and the optical density at 590 nm of the fermentation broth were also determined on an hourly basis.

Optical Density and Residual Glucose Concentration

Optical density was measured using the Pharmacia Ultrospec 4000 UV/Visible spectrophotometer set at 590 nm. Milli Q water was used to set the reference blank and for diluting the culture as required. Residual glucose concentration was estimated with a glucose Chemstrip BG from Boehringer Mannheim.

Temperature, pH, RPM and Aeration

Temperature and pH were measured directly inside the fermenter using a PT100 temperature probe and a Bradley James pH probe, respectively. RPM was measured directly off the agitation shaft of the fermenter. Aeration was measured using a rotameter.

Fermenter Harvest (Recovery of Supernatant)

Approximately 2 L of clarified fermentation broth (A) was obtained by centrifugation. This method was used because of the excessive amounts of antifoam required during the fermentation. For (B), (C), (D) and (E) 5 L of the fermentation broth was clarified by microfiltration, using the 0.2 micron A/G Technology hollow fiber filter. Before filtration was started, the medium was cooled down to about 10° C. Once cross-flow was established, the filtrate clamp was slowly released to give a filtrate flow of about 700 mL/min. The retentate was pumped back into the fermenter, while 5 L of the filtrate were collected in sterile bottles and stored immediately at −70° C.

SDS-PAGE, ELISA and ADP Ribosylation Activity Analyses

Time-course samples of the fermentation were immediately frozen in 2 mL aliquots in cryo vials at −70° C. and subsequently analysed by SDS-PAGE to confirm the presence of CRM107. Samples showing the CRM107 protein band were scanned with a Sharp JX-330 scanner to estimate the concentration of CRM107 in the fermentation broth. CRM107 concentration was also analysed by sandwich ELISA and ADP ribosylation activity was measured.

Results and Discussion

In this set of experiments, five different media experiments were compared, including the 0.8% glucose/2.5% maltose (A), 2.4 glucose (B), 1.5% glucose/2.4% maltose (C), 1.5% glucose (with cysteine; D), 1.5% glucose (with 1% yeast extract, E).

Growth of *Corynebacterium diphtheriae*

Figure 1B:
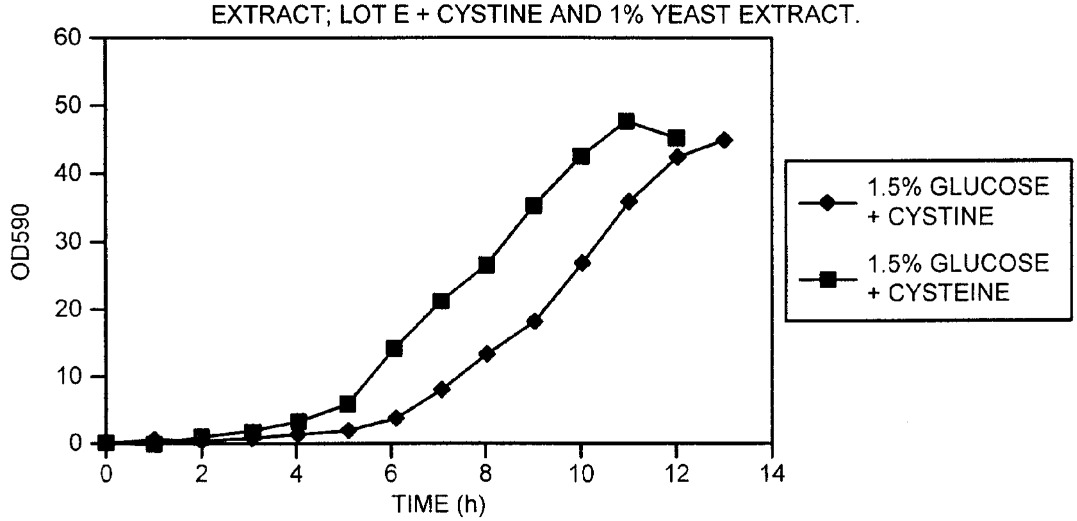
FIG. 1B shows the growth results of batch fermentation lots in media containing 2% yeast abstract and 0.26 g/l cysteine (D) and 1% yeast extract and 0.7 g/l cystine (E).

As shown in FIG. 1*a, C. diphtheriae* grew to a final $OD_{590}$ of 25 to 28 in 14 hours in the three batch fermentation processes. Growth was initially slower in the 2.4% glucose medium, which might have been due to a 'culture shock' following transfer of the innoculum from a medium without carbon source. Growth of *C. diphtheriae* in the two fed-batch fermentation processes was faster in the glucose+cysteine medium than in the glucose+cystine medium. However, the growth rate as well as the final $OD_{590}$ were essentially the same (FIG. 1*b*).

Production of CRM107

Figure 2:
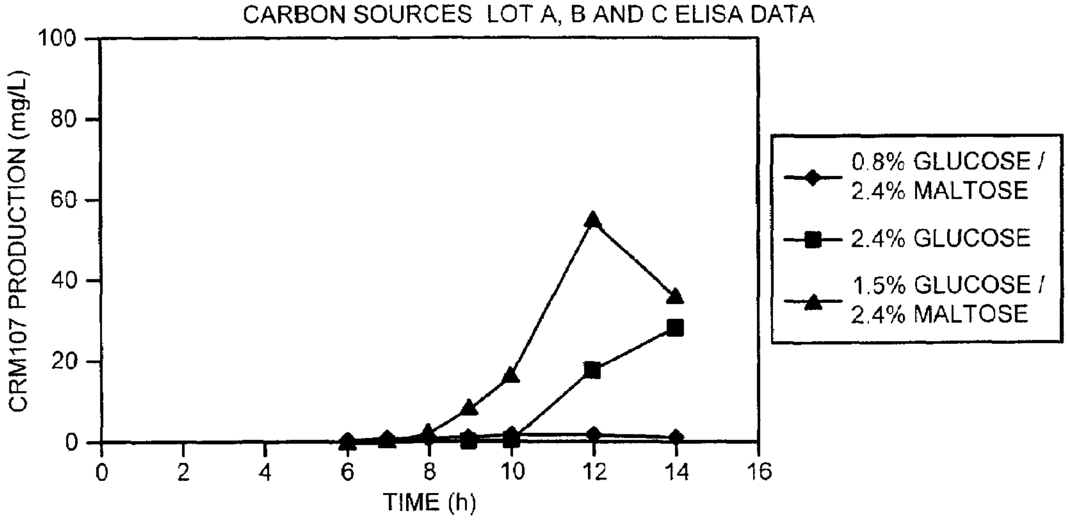
FIG. 2 shows CRM107 concentration post fermentation with conditions of (A), (B) and (C) measured by SDS-PAGE.

The production of CRM107 during the course of the fermentation was analysed both by SDS-PAGE, ELISA and ADP-ribosylation assay. In the three batch processes, the 1.5% glucose/2.4% maltose medium supported a yield of 5 S mg/L (ELISA data) after 12 hours of fermentation (FIG. 2), which was the highest production achieved for the Batch processes. The 2.4% glucose medium was trailing behind in both growth and CRM107 production, by approximately 4 hours, consequently the production was delayed. The long lag phase may be due to the culture shock due to the high glucose concentration in the medium, particularly when the inoculum was grown in the absence of a carbon source. Despite this delay production began at 12 hours and continued to 13 hours, and could have perhaps continued a while longer. This is evidenced by the continued increase in CRM107, concentration observed in the 0.2 μm fraction (see Table 1), reaching 47 mg/L (ELISA data), as the fermenter was allowed to run for an additional hour while the other fermenter was being harvested. The 0.8% glucose/2.4% maltose medium produced very little CRM107, despite that the cell yield was equivalent to that obtained with the other fermentation media. This may be due to excessive foaming encountered with this fermentation, which resulted in not only a high consumption of antifoam but also forced the dissolved oxygen to drop to nearly 0 for a 15 to 20-minute period, as the agitation was turned down to less than 100 rpm, may have played a role in the observed poor yield.

The CRM107 yield is significantly higher than that obtained from glycerol fermentation (data not shown), with an increase of approximately 14-fold in the post-fermentation CRM107 concentration as measured by SDS PAGE.

Figure 3:
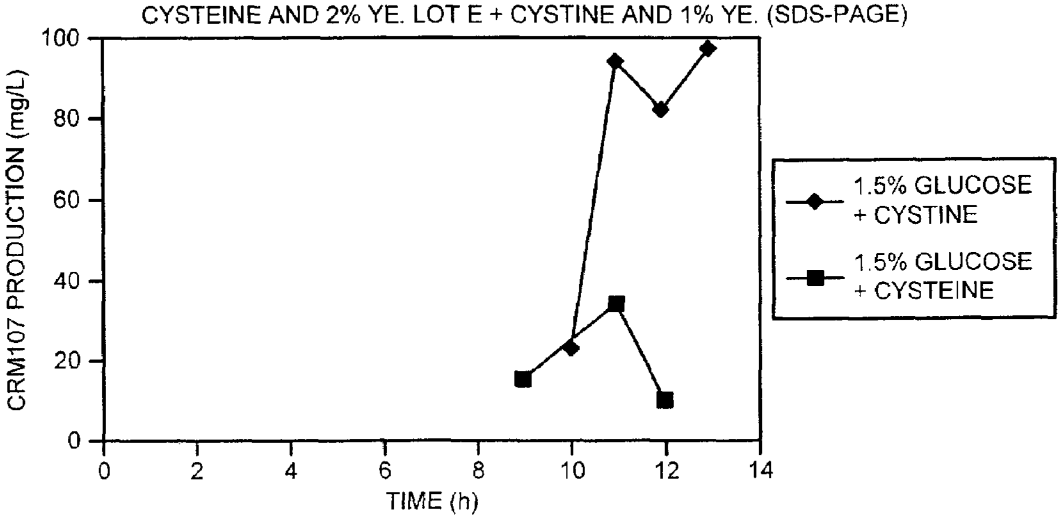
FIG. 3 shows CRM107 concentration post fermentation with conditions of (D) and (E) measured by ELISA.

In the fed-batch processes, the 1.5% glucose medium, with half the amount of yeast extract used in the other four media, proved to be the best overall medium for CRM107 production. The final yield approached 100 mg/L of CRM107 in 12 hours of fermentation (FIG. 3). Glucose feeding started at about 9.5 hours of fermentation and proceeded for 3.5 hours. A total of 125 g of glucose (251 mL of a 50% solution) was added to the fermenter as a means of controlling the pH, when acid was required later during the course of the fermentation (Table 2). The strategy for feeding glucose relied on the adjustment of pH by organic acids produced from glucose metabolism, instead of using inorganic acid.

We also analysed CRM107 concentration by the ADP-ribosylation assay. The results are shown in Table 3, comparing the concentration of CRM107 determined by ELISA and ADP-ribosylation assay. The product obtained is shown in the ADP-ribosylation assay to be biologically active. Glucose fed-batch (1.5% glucose) containing 1% yeast extract results in optimum toxin production.

Scale Up

We have scaled up this process based on the optimum conditions of fed glucose, 1% yeast extract to 50 l and observed that exponential growth, as in the 10 l culture, started around 6 hours and continued until 13 hours. After 14 hours, *C. diphtheriae* grew to an $OD_{590}$ of 37.4. CRM107 production as judged by SDS PAGE was 165.5 mg/l at the end of fermentation.

TABLE 2

Glucose feed during the Fed-batch fermentation of *C. diphtheriae*, Lots #D and E

| Fermentation Time (h) | Cumulative Amount of Glucose added (g/fermenter) D | E |
|---|---|---|
| 8.00 | 0.0 | 0.0 |
| 8.17 | 0.0 | 0.0 |
| 9.00 | 0.0 | 9.0 |
| 9.50 | 40.5 | 54.0 |
| 10.00 | 95.0 | 107.5 |
| 11.00 | 105.5 | 125.5 |

TABLE 3

ADP-ribosylation activity of CRM107 in the fermentation broth time course samples Lot #A, B and C

| Fermentation Samples | Fermentation Lot Number | CRM107 Concentration by ELISA (mg/L) | CRM107 Concentration by SDS-PAGE (mg/L) | CRM107 Concentration by ADP-Ribosylation (mg/L) |
|---|---|---|---|---|
| T = 12 | A | 1.2 | Und(1) | 3.21 |
| T = 14 | A | 0.8 | Und(3) | 0.86 |
| T = 12 | B | 17.4 | ND | 12.36 |
| T = 14 | B | 28.7 | 18.0 | 32.72 |
| 0.2 μm | B | 35 | 25.0 | 84.76 |
| T = 12 | C | 55.5 | 47.0 | 69.72 |

TABLE 1

Summary of the five optimisation fermentation processes

| | Lot A | B | C | D | E |
|---|---|---|---|---|---|
| Fermentation Process | Batch | Batch | Batch | Fed-Batch | Fed-Batch |
| Carbon source | 0.8% Glucose/2.5% Maltose | 2.4% Glucose | 1.5% Glucose/2.4% Maltose | 1.5% Glucose | 1.5% Glucose |
| Yeast extract | 20 g/L | 20 g/L | 20 g/L | 20 g/L | 10 g/L |
| Cystine/Cysteine | Cystine 0.7 g/L | Cystine 0.7 g/L | Cystine 0.7 g/L | Cysteine 0.26 g/L | Cystine 0.7 g/L |
| Initial pH | 7.21 | 7.17 | 7.22 | 7.17 | 7.24 |
| Final pH | 7.21 | 7.16 | 7.21 | 7.19 | 7.22 |
| Final OD | 25.4 | 27.8 | 26.8 | 45.3 | 45.3 |
| CRM107 concentration post fermentation measured by SDS-PAGE | 0 mg/L | 18.0 mg/L | 44.0 mg/L | 11.0 mg/L | 98.0 mg/L |
| CRM107 concentration post fermentation, measured by ELISA | 0.83 mg/L | 28.7 mg/L | 36.9 mg/L | 9.13 mg/L | 63.6 mg/L |
| CRM107 concentration post fermentation, measured by ADP-ribosylation assay | 0.86 mg/L | 32.72 mg/L | 70.88 mg/L | | |
| CRM107 concentration Post microfiltration, measured by SDS-PAGE | ND | 25.0 mg/L | 48.0 mg/L | 11.0 mg/L | 90.0 mg/L |
| CRM107 concentration Post microfiltration, measured by ELISA | ND | 47.0 mg/L | 29.9 mg/L | 4.73 mg/L | 108.8 mg/L |
| CRM107 concentration Post microfiltration, measured by ADP-ribosylation assay | ND | 84.76 mg/L | 90.76 mg/L | | 154.9 mg/L |

TABLE 3-continued

ADP-ribosylation activity of CRM107 in the fermentation broth time course samples Lot #A, B and C

| Fermentation Samples | Fermentation Lot Number | CRM107 Concentration by ELISA (mg/L) | CRM107 Concentration by SDS-PAGE (mg/L) | CRM107 Concentration by ADP-Ribosylation (mg/L) |
|---|---|---|---|---|
| T = 14 | C | 36.9 | 44.0 | 70.88 |
| 0.2 μm | C | 29.3 | 48.0 | 90.7 |

Und[(1)]: Undetectable.

EXAMPLE 2

Primary Recovery of CRM107 Produced from a Fermentation of *Corynebacterium diphtheriae* (β Tox$^{\pm}$)

CRM107 was recovered from fermentation broth by two steps. The first aims at clarifying the fermentation broth, using a 0.1 μm or 0.2 μm A/G Technology hollow fiber filter. The second step achieves an approximate 10-fold concentration of the cell-free fermentation broth, using a 30K A/G Technology hollow fiber membrane. This concentrated clarified fermentation broth is then used as the starting material for the purification of CRM107 (see Example 3).

This study investigates a number of recovery processes using the 0.1 μm filtrate from a 50-L glucose fed-batch fermentation as the starting material. The objective was to develop a process that minimizes product loss during primary recovery.

Procedure

Materials

The various filters tested in this study are listed in Table 4. They were tested for their efficiency during the ultrafiltration and diafiltration processes.

TABLE 4

Types of filters tested in the primary recovery optimization study

| Membrane types | Cat # | Characteristic |
|---|---|---|
| AMICON MiniPlate-10 | 1571303 | 10,000NMWC flat plate |
| AMICON MiniPlate-30 | 1571304 | 30,000NMWC flat plate |
| FILTRON 10K Alpha | AS010C72 | 10,000NMWC flat plate |
| AIG Technology 1 OK | UFP-10-C-6A | 10,000NMWC hollow fiber |
| AIG Technology 30K | UFP-30-C-6A | 30,000NMWC hollow fiber |
| FILTRON 10K Omega series | 0501070 | 10,000NMWC flat plate |

Fermentation Broth Clarification

The fermentation broth used to optimize the primary recovery of CRM107 was obtained from a 50-L glucose fed-batch fermentation of *C. diphtheriae* (β tox$^{+}$), as in Example 1. Twenty liters of the fermentation broth was clarified using the 0.1 μm A/G Technology hollow fiber filter.

Primary Recovery Schemes

Six primary recovery schemes (as summarized in Table 5) were evaluated using the 0.1 μm filtrate as the starting material.

TABLE 5

CRM107 primary recovery optimization schemes

| | | Primary recovery optimization schemes | | | | | |
|---|---|---|---|---|---|---|---|
| Step # | Filtration type | Scheme #1 | Scheme #2 | Scheme #3 | Scheme #4 | Scheme #5 | Scheme #6 |
| 1 | Microfiltration | 0.1 μm hollow fibre | | | | | |
| 2 | Ultrafiltration | 30K A/GT hollow fibre | 30K A/GT hollow fibre | 30K Amicon flat plate | 10K Amicon flat plate | 10K Filtron alpha flat plate | 30K A/GT hollow fibre |
| 3 | Diafiltration | 30K A/GT hollow fibre | 10K A/GT hollow fibre | 30K Amicon flat plate | 10K Amicon flat plate | 10K Filtron alpha flat plate | 30K A/GT hollow fibre |

Primary Recovery Schemes #1 and 2

In scheme #1 12 L of the 0.1 μm filtrate was concentrated to 1.2 L using a 30K A/GT hollow fiber. This retentate was then divided into two equal batches of 550-mL, which had a starting conductivity of 16.8 mS/cm. In scheme #1, one 550-mL batch was diafiltered using a 30K A/GT hollow fiber filter, and the volume kept at approximately 500-mL with constant addition of 10 mM phosphate buffer. The diafiltration was stopped when the conductivity of the retentate was less than 5 mS/cm (4.34 mS/cm). A total of approximately 2 L of permeate was collected.

In scheme #2, the other 550-mL batch was diafiltered using a 10K A/GT hollow fiber filter, and the volume kept at approximately 500 mL with constant addition of 10 mM phosphate buffer. Diafiltration was stopped when the conductivity of the retentate was less than 5 mS/cm (3.97 mS/cm). A total of approximately 2 L of permeate was collected. The aim of scheme #2 was to minimize CRM107 loss during diafiltration. Diafiltration was to reduce salt interference during later stages of purification (such as ion exchange chromatography).

Primary Recovery Schemes #3, 4, 5 and 6

These four schemes were based on the use of Amicon and Filtron flat plate tangential flow filters for the concentration and diafiltration steps. Schemes 3, 4 and 6 were to evaluate different membrane chemistries.

In scheme #3, 950 mL of the 0.1 μm filtrate was concentrated to approximately 125 mL using a 30K Amicon tangential flow filter. The conductivity of the retentate was 18.6 mS/cm. The retentate was brought up to approximately 200 mL with 10 mM phosphate buffer, and then diafiltered using the same filter. The volume was kept at approximately 200 mL with constant addition of 10 mM phosphate buffer. Diafiltration was stopped when the conductivity of the retentate was reduced to less than 5 mS/cm (4.34 mS/cm). A total of approximately 600 mL of permeate was collected. The final retentate volume was 75 mL.

In scheme #4, 550-mL of the 0.1 μm filtrate was concentrated down to approximately 100 mL using a 10K Amicon tangential flow filter. The conductivity of the retentate was 18.5 mS/cm. The retentate was brought up to approximately 200 mL with 10 mM phosphate buffer, and then diafiltered using the same filter. The volume was kept at approximately 200 mL with constant addition of 10 mM phosphate buffer. Diafiltration was stopped when the conductivity of the retentate was less than 5 mS/cm (4.43 mS/cm). A total of approximately 500 mL of permeate collected. The final retentate volume was 83 mL.

In scheme #5, 950 mL of the 0.1 μm filtrate was concentrated down to approximately 150 mL using a 10K Filtron alpha tangential flow filter. The conductivity of the concentrate was 17.2 mS/cm. The retentate was brought up to approximately 200 mL with 10 mM phosphate buffer, and then diafiltered using the same filter. The volume was kept at approximately 200 mL with constant addition of 10 mM phosphate buffer. Diafiltration was stopped when the conductivity of the retentate was less than 5 mS/cm (3.80 mS/cm). A total of about 800 mL of permeate was collected. The final retentate volume was 72 mL.

In scheme #6, approximately 18 L of the 0.1 μm filtrate was concentrated to approximately 1.8 L using a 30K hollow fiber filter. The retentate was diafiltered using a 10K omega Filtron tangential flow membrane. The volume was kept constant at approximately 400 mL with constant addition of 10 mM potassium phosphate buffer. The diafiltration was stopped when the conductivity was less than 5 mS/cm (4.74 mS/cm).

Primary Recovery Sample Analysis

The primary recovery optimization was using 1.8 mL samples taken at the start and end of the process for analysis of CRM 107 recovery and process efficiency. Samples were immediately frozen in cryogenic vials at −70±5° C. and subsequently analyzed by SDS-PAGE, isoelectric focussing, Western blot, and HP-SEC.

SDS-PAGE and Western Blot

SDS-PAGE and Western blot analysis of the samples were carried on a Bio-Rad precast 4-15% polyacrylamide gradient gel. Samples were diluted 1-2 fold in phosphate buffered saline (for the permeate and 0.1 μm filtrate samples), or 20 fold (for the retentate), and then an additional two fold in the solubilization buffer solution. Twenty microliters of the mixture were loaded on a gel, and electrophoresed at 200 V for 50 min. Samples showing the CRM107 protein band on SDS-PAGE were scanned with a Sharp JX-330 scanner to estimate the concentration of CRM107. For Western blot analysis, the protein bands on the polyacrylamide gel were transferred onto a nitrocellulose membrane and probed with mouse anti-human diphtheria toxin, and detected with anti-mouse IgG alkaline phosphatase conjugate.

Isoelectric Focussing (IEF)

IEF analysis of the retentate samples was carried out using the Pharmacia Ampholine PAG plate (pI 4-6.5), with pI markers ranging from 3.6-6.6. Samples were appropriately diluted between 1 to 5 fold. Twenty microliters of the mixture were loaded on a gel, and electrophoresed at a voltage of 2000 V, at 25 mA, for 2.5 h.

High Performance Size Exclusion Chromatography (HP-SEC)

The final samples of the recovery optimization process, obtained after the diafiltration step, were analyzed by HP-SEC to evaluate the degree of purity of the product and the impact of the process on pigment removal. One hundred microliters of the samples were loaded on the column and the chromatograph monitored at a wavelength of 280 nm. The CRM107 peak eluted with a retention time of about 9.3 min. The % peak area was used to estimate product purity.

Results and Discussion

Six optimization schemes of CRM107 primary recovery were evaluated for product recovery and process efficiency in facilitating the subsequent purification of CRM107. The criteria applied for the primary recovery were (i) to achieve a 5-10 fold concentration of the 0.1 μm-clarified fermentation broth with an ultrafiltration step, and (ii) to reduce the conductivity of the concentrated broth to below 5 mS/cm with a diafiltration step.

The optimization study was monitored using four different analyses (SDS-PAGE, Western blot, IEF and HP-SEC). Western blot and IEF data showed the presence of CRM107 in all retentate samples. Similarly, the SDS-PAGE data showed CRM107 in the retentate samples, as well as in the 0.1 μm filtrate sample (Table 6). Analysis of the permeate samples by SDS-PAGE suggest that all schemes tested, except for scheme #1 and 5, did not cause any noticeable loss of CRM107 in the permeate. On the basis of SDS-PAGE, IEF and HP-SEC data, scheme #3 appears to be the primary recovery process of choice. The SDS-PAGE data do not support this conclusion as the recovery post-diafiltration is good in most cases, except for scheme #5, where noticeable loss of product was evident. Data from IEF show more bands in the sample processed by scheme #5, implying that this diafiltered sample was the least clean. In all samples analyzed by IEF, three prominent bands were visible, identical to those present in the reference standard sample, with a pI between 5.0 and 5.4.

The purity achieved with scheme #3 after this step was 17.5% compared to 9% CRM107 purity with scheme #1, Table 4. The recovery of CRM107 is best with scheme #3, which showed a CRM107 peak area of 161, nearly 2-fold greater than that from scheme #1.

TABLE 6

Material balance of the different primary recovery schemes (SDS-PAGE data)

| Filtration Step | Primary Recovery Scheme 1 | 2 | 3 | 4 | 5 | 6 |
|---|---|---|---|---|---|---|
| Microfiltration | | | | | | |
| Filtrate CRM107 conc. (g/L) | 0.113 | 0.113 | 0.102 | 0.113 | 0.114 | 0.113 |
| Filtrate volume (L) | 6.0 | 6.0 | 0.950 | 0.550 | 0.950 | 18.0 |
| Filtrate CRM107 total amount (mg) | 678.0 | 678.0 | 96.9 | 62.3 | 108.3 | 2034 |
| Ultrafiltration | | | | | | |
| Retentate CRM107 conc. (g/L) | 1.055 | 1.055 | 1.067 | 0.375 | 0.445 | |
| Retentate volume (L) | 0.550 | 0.550 | 0.125 | 0.100 | 0.150 | |
| Retentate CRM107 total amount (mg) | 580.3 | 580.3 | 133.4 | 37.5 | 66.8 | |
| Ultrafiltration | | | | | | N/A |
| Filtrate CRM107 conc. (g/L) | 0.012 | 0.012 | 0 | 0 | 0.041 | |
| Filtrate volume (L) | 5.45 | 5.45 | 0.825 | 0.450 | 0.800 | |
| Filtrate CRM107 total amount (mg) | 65.4 | 65.4 | 0 | 0 | 32.8 | |
| Diafiltration | | | | | | |
| Retentate CRM107 conc. (g/L) | 1.396 | 1.197 | 1.271 | 0.834 | 0.358 | 3.429 |
| Retentate volume (L) | 0.5 | 0.5 | 0.075 | 0.083 | 0.072 | 0.400 |
| Retentate CRM107 total amount (mg) | 698 | 598 | 95.3 | 69.2 | 25.8 | 1372 |
| Diafiltration | | | | | | |
| Filtrate CRM107 conc. (g/L) | 0 | 0 | 0 | 0 | 0.031 | |
| Filtrate volume (L) | 2 | 2 | 0.6 | 0.5 | 0.8 | N/A |
| Filtrate CRM107 total amount (mg) | 0 | 0 | 0 | 0 | 24.8 | |
| Microfiltration | | | | | | |
| Filtrate CRM107 total amount (%) | 100 | 100 | 100 | 100 | 100 | 100 |
| Ultrafiltration | | | | | | |
| Retentate CRM107 total amount (%) | 85.5 | 85.5 | 137.1 | 61.2 | 62.0 | N/A |
| Ultrafiltration | | | | | | |
| Filtrate CRM107 total amount (%) | 0 | 0 | 0 | 0 | 30.6 | |
| Diafiltration | | | | | | |
| Retentate CRM107 total amount (%) | 102.9 | 88.2 | 97.4 | 113.6 | 24.1 | 67.5 |
| Diafiltration | | | | | | |
| Filtrate CRM107 total amount (%) | 0 | 0 | 0 | 0 | 23 | N/A |

TABLE 7

HP-SEC analysis of diafiltration samples from the different primary recovery schemes

| Diafiltration Step | Primary Recovery Scheme 1 | 2 | 3 | 4[(1)] | 5 | 6 |
|---|---|---|---|---|---|---|
| Retentate CRM107 amount (peak area)[(1)] | 96.5 | 77.6 | 161.2 | 88.3 | 58.1 | 642.0 |
| Retentate CRM107 amount (% total peak area) | 9.0 | 8.8 | 17.5 | 6.6 | 4.8 | 22.19 |
| Retentate CRM107 conc. by SDS-PAGE (g/L) | 1.396 | 1.197 | 1.271 | 0.834 | 0.358 | 3.429 |

[(1)]100 μL samples were loaded on the column

EXAMPLE 3

Purification of CRM107 with Ion Exchange Chromatography and Hydrophobic Interaction Chromatography

Background

CRM107 purification protocol has traditionally involved two chromatographic processes. First is HIC which leads to the greatest fold-purification, removing most of the contaminating pigment in the process, but has the disadvantage of the greatest drop in yield. Next, after concentration and exchange into the appropriate buffer via diafiltration, an IEC step is performed to further clean the product; the loss in yield is not as dramatic but neither is the degree of purification.

This study reverses these two chromatographies to determine if an improvement could be made in either yield or purity without adverse effects, the rationale being that not only would the IEC procedure act as a gross scrubbing step for the HIC run but it would also be more amenable to the increased sample volume anticipated with large scale fermentations of 50 L.

Materials and Methods

1. Preparation of Samples

A crude, frozen preparation of CRM107 consists of 20 L of cell free fermentation broth from a 50 L fermentation concentrated across a 30K hollow-fibre filter to yield 2 L of retentate. This was diafiltered further (using a 10K Omega Ultrasette) to equilibrate the pH and conductivity with Buffer C (10 mM Potassium Phosphate, pH 7.6±0.2); the resulting 400 mL retentate was split into 200 mL aliquots for storage at −70° C. Prior to the initial chromatographic step each lot was thawed at approximately 27° C.; hereafter the procedures differ.

The sample purified according to the traditional protocol is referred to as LOT A while the one subjected to the alternate procedure is labelled LOT B.

(A) The 200 mL of retentate was conditioned for HIC by adding 30 g of $(NH_4)_2SO_4$ with stirring. This material was then passed through a 0.22μ filter (Media-Kap 25) to remedy its cloudiness prior to loading onto the HIC column.

(B) 500 mL of Buffer C was added to 200 mL of retentate in order to adjust the loading to be identical to that of the IEC step of Lot A (see Section 3). No filtration was necessary.

2. First Chromatographic Procedure (A) Hydrophobic Interaction Chromatography Using Decyl Agarose 6XL.

A column of Decyl Agarose 6XL column volume $\{V_c\}$ ~250 mL) was equilibrated with Buffer A (50 mM Potassium Phosphate, 1 M $(NH_4)_2SO_4$, pH 7.0±0.2) prior to loading of the filtrate obtained after the 0.22 μm filtration. After loading the column was washed with four $V_c$ of Buffer A, followed sequentially by five $V_c$ of Buffer B (50 mM Potassium Phosphate, pH 7.0±0.2) at each of 30% B, 50% B, and 100% B. CRM107 was eluted during the 30% B step and its purity was measured as 55.1% by HP-SEC. All pools were stored @ 2-8° C. pending further processing.

(B) Ion Exchange Chromatography Using Pharmacia DEAE Fast Flow.

A Pharmacia DEAE FF column ($V_c$~220 mL) was equilibrated with Buffer C prior to loading the 700 mL sample. It was then washed with four $V_c$ of Buffer C. Bound CRM107 was eluted with a linear gradient of 0-50% Buffer D (10 mM Potassium Phosphate, 500 mM KCl, pH 7.6±0.2) carried out over ten $V_c$ with concurrent collection of 90 mL fractions. It was then washed with five $V_c$ of 100% D. After HP-SEC analysis, it was decided to pool fractions 12-16; the resulting purity was approximately 69.8% (calculated from the Peak Area and Area Percent of each fraction). Each pool/fraction was collected and stored @ 2-8° C. until further processing.

3. Diafiltration & Concentration Using 10K Omega Ultrasette (A) The 1300 mL pool of CRM107 from the HIC step (the 30% B fraction) was diafiltered using a 10K Omega Ultrasette membrane. Diafiltration was carried out using Buffer C until the conductivity of the pooled sample fell to ≦5 mS/cm; 3900 mL of diafiltration buffer was required to reach a conductivity of 4.34 mS/cm and a final retentate volume of 700 mL. The purity of CRM107 in the retentate was measured as 79.3% by HP-SEC. The pools were stored @ 2-8° C. until further processing.

(B) The 450 mL pool of CRM107 from the DEAE step (fractions 12-16) was diafiltered using a 10K Omega Ultrasette membrane. Diafiltration was carried out using Buffer A until the conductivity of the pooled sample rose to 130±20 mS/cm; 600 mL of diafiltration buffer was required to reach a conductivity of 116 mS/cm and a final volume of 300 mL. The purity of CRM107 in the retentate was measured as 84.2% by HP-SEC. The pools were stored @ 2-8° C. until further processing. The solution remained clear throughout this step.

4. Second Chromatographic Procedure (A)—Ion Exchange Chromatography Using Pharmacia DEAE Fast Flow.

A Pharmacia DEAE FF column ($V_c$ ~220 mL) was equilibrated with Buffer C prior to loading the 700 mL sample. It was then washed with four $V_c$ of Buffer C. Bound CRM107 was eluted with a linear gradient of 0-50% Buffer D carried out over ten $V_c$ with concurrent collection of 90 mL fractions. It was then washed with five $V_c$ of 100% D. After HP-SEC analysis, it was decided to pool fractions 15 & 16; the resulting purity is 94.9% (95.6% if calculated from the Peak Area and Area Percent of each fraction as per Section 2, LOT B). Each pool/fraction was collected and stored @ 2-8° C. until further processing.

(B)—Hydrophobic Interaction Chromatography Using Decyl Agarose 6XL

A column of Decyl Agarose 6XL ($V_c$~220 mL) was equilibrated with Buffer A prior to loading of the 300 mL sample. After loading the column was washed with four $V_c$ of Buffer A, followed sequentially by five $V_c$ of Buffer B at each of 30% B, 50% B, and 100% B. CRM107 was eluted during the 30% B step and its purity was measured as 76.6% by HP-SEC. All pools were stored @ 2-8° C. pending further processing.

5. Second Diafiltration & Concentration Using 10K Cutoff (A) Buffer C was used to equilibrate a 150 mL Filtron stirred-cell unit containing a 10K Omega membrane, pressurized to 40-45 psi. This was used to diafilter the 180 mL DEAE pool. 260 mL of Buffer C was used to yield 31 mL of retentate with a final purity of 98.0% as monitored by HP-SEC. The HP-SEC profile had no detectable peaks with retention times between 10 and 11 minutes.

(B) The 1100 mL HIC pool was first concentrated using the 10K Omega Ultrasette; 670 mL of Buffer C was used to bring the retentate volume down to 150 mL. This was further concentrated to 34 mL with the prepared 150 mL Filtron stirred-cell unit containing a 10K Omega membrane. The final purity was 97.4% as monitored by HP-SEC. The HP-SEC profile showed two peaks at 10.2 and 10.6 minutes which account for 1.4% of the Area Percent.

Results and Discussion

To determine the efficiency of each step, various in-process samples were analysed by some or all of the following techniques: HP-SEC, SDS-PAGE, IEF, Protein-dye (Coomassie) absorbance, intrinsic absorbance at 280 nm, & DNA-dye fluorescence. These data are summarised in Tables 8 and 9.

Whilst the procedures do appear to differ in their overall percent recoveries this is partially an artifact of the excessive backpressure applied to the Ultrasette diafiltration step performed on Lot A. Consequently, about 60% (160 mg) of the CRM107 fraction from the HIC step was lost to the filtrate, compared to only 8% for Lot B. All else being equal, when this loss is factored in Lot A should have had an overall recovery of 27% (160 mg), more on par with Lot B. Even with this irregularity accounted for, the overall yield for Lot A is still only 70% of that obtained with Lot B.

TABLE 8

Yield, purity and recovery data for Lots A and B

| Step | A Yield (mg) | A Step Recovery (%) | A HP-SEC Purity (% Area) | B Yield (mg) | B Step Recovery (%) | B HP-SEC Purity (% Area) |
|---|---|---|---|---|---|---|
| Crude CRM107 | 600 | N/A | 22.2 | 600 | N/A | 22.2 |
| Preparation for Chromatography | 400 | 67 | 21.1 | 600 | 100 | 17.8 |
| 1st Chromatography Pool[1] | 270 | 68 | 55.1 | 400 | 67 | 69.8 |
| Ultrasette Pool | 85 | 31‡ | 79.3 | 370 | 92 | 84.2 |
| 2nd Chromatography Pool[2] | 37 | 44 (54)* | 94.9 | 130 | 35 (57)* | 76.6 |
| Stirred Cell (Final Product) | 46 | 124 | 98.0 | 210 | 163 | 97.4 |
| Overall Recovery | | 7%[27%]‡ | | | 35% | |

‡The Ultrasette was subjected to excessive backpressure during this step as evidenced by the amount of CRM107 in the filtrate (156 mg, ~60% of the HIC pool); during B only 30 mg (8% of the DEAE pool) was similarly lost. Taking this loss into account, the overall recovery for Lot A is 27%
*These values were calculated using stirred cell yields

TABLE 9

Results for Purification of CRM107 from Lots #A and B

| Sample | A Crude CRM107 | A HIC Pool | A Ultrasette Pool | A DEAE Pool | A Stirred Cell | B Crude CRM107 | B DEAE Pool | B Ultrasette Pool | B HIC Pool | B Stirred Cell |
|---|---|---|---|---|---|---|---|---|---|---|
| CRM107 yield by absorbance at 280 nm | Not determined due to interfering species | | | | 45 mg | Not determined due to interfering species | | | | 180 mg |
| CRM107 yield by Coomassie dye-binding | | | | | 35 mg | | | | | 160 mg |
| [DNA] (ng/mL) | N.D. | 800 | 280 | <LOD | <LOD | N.D. | <LOD | <LOD | <LOD | <LOD |
| IEF | Indistinguishable from the 0.4 g/L CRM107 Standard | | | | | Indistinguishable from the 0.4 g/L CRM107 Standard | | | | |

Note:
The LOD (Limit of Detection) for the DNA assay is 5 ng/mL

This discrepancy between the two overall recoveries is undoubtedly directly attributed to the different processes used to prepare the samples for the first chromatography step. In Lot A, the additional $(NH_4)_2SO_4$ and filtration steps led to the loss of 200 mg of the CRM107 present in the culture supernatant.

CRM107 produced from Lot B by performing IEC before HIC led to an increase in the amount recovered from the concentrated broth.

EXAMPLE 4

Expression of CRM107 in *Escherichia coli*

This was to study the expression of the diphtheria toxin mutant CRM107 a different microbial host. DNA was purified from corynebacteriophage β isolated from cultures *C. diphtheriae*, and a 2 kb fragment containing the entire gene encoding CRM107 including the promoter and the signal sequence was inserted into the polylinker cloning site of pUC19 and amplified in *Escherichia coli*. CRM107 was expressed in different *E. coli* strains and accumulated in the periplasm of the bacteria. The expression level was up to 45 mg recombinant protein per litre medium.

Materials and Methods

Strains and plasmids: *Corynebacterium diphtheriae* C7($\beta^{tox\text{-}107}$) was received from Dr. Richard Youle, NIH, and was used for production of CRM107. *C. diphtheriae* C7(−) (ATCC 27010) was used for amplification and titration of β-phages.

The plasmid pUC19 (Gibco, Paisley, UK) was used as vector for cloning of the CRM107 gene and *E. coli* DH5α (Gibco), *E. coli* HB2151 (Pharmacia Biotech, Uppsala, Sweden), *E. coli* TG1 (Pharmacia Biotech) and *E. coli* RR1ΔM15 (ATCC 35102) were used for expression of CRM107.

Preparation of β-phage: DNA was prepared as described by Greenfield, L., Bjorn, M. J., Horn, G. Fong, D., Buck, G. A., Collier, R. J. and Kaplan D. A. (1983) *Proc. Natl Acad Sci*

*USA* 80, 6853-6857 with minor modifications. Briefly, β-phages were isolated from the medium of *C. diphtheriae* C7($\beta^{tox-107}$) and amplified in *C. diphtheriae* C7(−). The cells were removed by centrifugation at 2500 g, and the medium was further clarified by centrifugation at 1500 g. Polyethylene glycol 8000 and NaCl were added to concentration of 6% and 0.5 M, respectively, to the phage-containing supernatant. The phages were precipitated by incubation on ice for 2 hours and recovered by centrifugation at 15000 g for 20 min.

Titration of phages to determine the number of plaque forming units (pfu) was performed in *C. diphtheriae* C7(−) as described in Laird, W and Groman, N. (1976) *J. Virol* 19, 208-219.

The phages ($10^{11}$ pfu) suspended in 100 mM Tris-HCl, pH 7.5, 100 mM NaCl, 25 mM EDTA were incubated with 1 mg/ml pronase (Sigma, St. Louis, Mo.) for 2 hours at 37° C. and then extracted with an equal volume of phenol:chloroform:isoamylalcohol (49.5:49.5:1). The aqueous phase was precipitated with cold ethanol after addition of Na-acetate to a concentration of 0.3 M. The pellet was washed once with 70% ethanol and dissolved in 10 mM Tris-HCl, pH 7.5, 1 mM EDTA.

Cloning of CRM107 into pUC19. Purified β-DNA was cleaved with EcoRI and XbaI and separated in 1% agarose gel. A band of 2 kb was excised from the gels and purified using a QIAEXII Agarose Gel Extraction Kit (Qiagen GmbH, Hilden, Germany). The isolated fragment was ligated into the polylinker cloning site of pUC19. Restriction enzymes (New England Biolabs, Beverly, Mass.) and T4 ligase (Pharmacia Biotech) were used according to the suppliers recommendations. The resulting plasmid, pEtox, was amplified in *E. coli* TG1.

Expression of CRM107 in *E. coli*: The plasmid pEtox was transformed to different *E. coli* strains by electroporation. The bacteria are grown at 37° C. in accordance with the invention. The cells are harvested by centrifugation, and whole cell extracts made by disintegration of the cells in a French Press. Fractionation of the cells was performed by first isolating the periplasma proteins from freshly grown cells by osmotic shock. Nossal, N. G. and Heppel, L. A. (1966) *J. Biol Chem* 241, 3055-3062. The residual was disintegrated in a French Press, and the membrane fraction separated from the cytoplasma by centrifugation.

EXAMPLE 5

Conjugation of Transferrin with CRM107

CRM107 was conjugated with transferrin according to published methods, including the method described in U.S. Pat. No. 5,728,383.

Substitution of CRM107:

150 mg of CRM107 (concentration of approximately 10 mg/ml) was mixed with 299 μl of MBS solution (10 mg/ml) and incubated at room temperature for 30 minutes. The amount of MBS added was a 3.5 times molar excess of CRM107. Upon completion of the incubation, the reaction was quenched by placing the mixture at 5° C., followed by desalting on a Sephadex G25 column.

Substitution of Transferrin:

350 mg of transferrin (concentration approximately 20 mg/ml) was mixed with 840 μl 2-IT (5 mg/ml) and incubated at 37° C. for 30 minutes. The amount of 2-IT added was 7.7 times molar excess of transferrin. Upon completion of the incubation the reaction was quenched by placing the mixture at 5° C. followed by desalting on a Sephadex G25 column.

Conjugation of Substituted Transferrin and CRM107:

The MBS substituted CRM107 (141 mg) and 2-IT substituted transferrin (293 mg) in the ratio of 1:2 were mixed together and incubated at 5° C. for 18 hours. Upon completion of the conjugation the conjugated was purified by ion exchange chromatography using Q Sepharose Fast Flow followed by gel filtration on Superdex 200 column.

Anion Exchange Chromatography of Conjugate:

Approximately 440 mg of conjugate was loaded onto 100 ml Q Sepharose Fast Flow column, equilibrated with sodium phosphate (0.05M) buffer at pH 7.6. The conjugate was eluted with 300 ml (3 column volumes) of elution buffer consisting of 70% equilibration buffer and 30% Buffer B (0.1M sodium phosphate, 1.5M sodium chloride pH 7.4). The conjugate peak was eluted between 60 ml and 150 ml of elution buffer.

Concentration of Conjugate:

Fractions from the Q Sepharose Fast Flow column which contained the conjugate were pooled and concentrated to a concentration greater than 10 mg/ml and loaded onto a Superdex 200 molecular sieve column for further purification. Equilibration and elution buffer for the Superdex 200 was 0.01M sodium phosphate pH 7.4 containing 0.15M sodium chloride. Purified conjugate was stored at −70° C.

What is claimed is:

1. A method for preparing a diphtheria toxin conjugate comprising conjugating a diphtheria toxin with one of a cell specific binding and targeting moiety, wherein said diphtheria toxin is produced by the steps of fermenting a microorganism capable of producing diphtheria toxin using glucose as a carbon source and adding glucose to a growing culture whereby the addition of glucose maintains a microorganism growth effective to support diphtheria toxin production, wherein the fermentation medium comprises from about 0.5 to about 1.5% yeast extract.

2. The method as claimed in claim 1 wherein the cell specific binding or targetting moiety is transferrin.

* * * * *